United States Patent [19]
Gentile et al.

[11] Patent Number: 5,895,789
[45] Date of Patent: Apr. 20, 1999

[54] PARENTERAL PHARMACEUTICAL COMPOSITIONS CONTAINING AMMONIOMALKYL SALTS OF 2-ARYLPROPIONIC ACIDS

[75] Inventors: Marco Gentile; Luigi Boltri, both of L'Aquila; Gaetano Clavenna, Milan, all of Italy

[73] Assignee: Dompe' SpA, L'Aquila, Italy

[21] Appl. No.: 08/894,733

[22] PCT Filed: Dec. 23, 1996

[86] PCT No.: PCT/IB96/01461

§ 371 Date: Aug. 27, 1997

§ 102(e) Date: Aug. 27, 1997

[87] PCT Pub. No.: WO97/24114

PCT Pub. Date: Jul. 10, 1997

[30] Foreign Application Priority Data

Dec. 28, 1995 [IT] Italy ............................. MI95A2777

[51] Int. Cl.⁶ ............................. A61K 31/19; A61K 31/38
[52] U.S. Cl. ............................. 514/570; 514/569; 514/448
[58] Field of Search ............................. 514/255, 448, 514/569, 570

[56] References Cited

U.S. PATENT DOCUMENTS

| | | | |
|---|---|---|---|
| 4,877,620 | 10/1989 | Loew et al. | 424/451 |
| 5,206,262 | 4/1993 | Donati et al. | 514/428 |

FOREIGN PATENT DOCUMENTS

| | | |
|---|---|---|
| 0 70 714 A1 | 1/1983 | European Pat. Off. |
| 0 136 470 A2 | 4/1985 | European Pat. Off. |
| 25 08 895 A1 | 9/1975 | Germany. |
| 2 059 768 | 4/1981 | United Kingdom. |
| WO 89/04658 | 6/1989 | WIPO. |
| WO 93/16689 | 9/1993 | WIPO. |
| WO 93/17677 | 9/1993 | WIPO. |
| WO 94/20449 | 9/1994 | WIPO. |

OTHER PUBLICATIONS

Chemical Abstracts, vol. 91 (1981) CA94: 162745 q.

*Primary Examiner*—Phyllis G. Spivack
*Attorney, Agent, or Firm*—Armstrong, Westerman Hattori, McLeland, & Naughton

[57] ABSTRACT

A pharmaceutical composition for parenteral administration having anti-inflammatory and analgesic properties is disclosed which contain, as the active principle, alkylammonium salts of 2-arylpropionic acids.

10 Claims, No Drawings

PARENTERAL PHARMACEUTICAL COMPOSITIONS CONTAINING AMMONIOMALKYL SALTS OF 2-ARYLPROPIONIC ACIDS

This application is a 371 of PCT/IB96/01461 filed Dec. 23, 1996.

The object of the present invention consists of pharmaceutical compositions suitable for parenteral administration which contain alkylammonium salts of 2-arylpropionic acids.

In particular, although the parenteral pharmaceutical compositions of the invention are suitable to be obtained with any 2-arylpropionic acid having antiinflammatory activity, they preferably contain, as 2-arylpropionic acid, ketoprofen or 3-benzoyl-α-methylbenzeneacetic acid, ibuprofen or 2-(4-isobutylphenyl)propionic acid, naproxen or (S)-6-methoxy-α-methyl-naphthaleneacetic acid and tiaprofenic acid or 5-benzoyl-α-methyl-2-thiopheneacetic acid, the ketoprofen being the 2-arylpropionic acid particularly preferred.

One of the advantages of the pharmaceutical compositions of the invention is that it allows for the administration of the non-steroid antiinflammatory substance by a route of administration, the parenteral one, which does not show side effects as shown by the pharmaceutical forms administered by topical route such as, for example, creams, lotions, gels or ointments which, because of their easy methods of application, are widely used. It is in fact known from literature on the subject that topical administration of non-steroid anti-inflammatory drugs can, in a more or less serious manner, provoke damage to the patient's skin due to the photolability of the drug which, in the presence of light, undergoes a degradation process, the products of which interfere negatively on the cellular membrane by the formation of free radicals.

The pharmaceutical compositions of the invention represent, moreover, a notable improvement as far as stability and convenience of use and safety are concerned with respect to the compositions already on the market containing the same anti-inflammatory drugs.

A decisively more advantageous aspect of said pharmaceutical compositions is that their administration causes uneasiness which is tolerable, compared to the pain, sometimes intense, caused by the compositions for parenteral use on the market containing the same anti-inflammatory drugs.

In particular, as far as ketoprofen is concerned, the relatively small side effects and the recognised effectiveness in the symptomatic treatment of rheumatoid arthritis, in osteoarthritis, in anchylosing spondylitis, of acute painful articular and periarticular symptoms of the musculoskeletal system, in gout and in dysmenorrhea, in the treatment of pain and inflammation which accompanies or follows orthopedic operations, have made such a drug one of the most frequently used active principles in oral administration among anti-inflammatory non-steroid drugs of current therapeutical use.

The analgesic and anti-inflammatory effect of ketoprofen has been, in a large measure, correlated to its capacity, or more specifically, to the capacity of its S-enantiomer, to inhibit the synthesis of prostaglandin. More recently, it has been recognised that the R-enantiomer, which in human beings does not undergo an appreciable metabolic conversion in the S-antipode, has its own analgesic property, mediated by mechanisms of action which, even though not fully clarified, seem to be completely independent from the prostaglandin synthesis block.

Pharmaceutical formulations for parenteral use containing as active principle ketoprofen and/or its enantiomers are thought to be particularly useful in the treatment of acute exacerbations of painful manifestations and as adjuvant in the symptomatic therapy of pain in persons suffering from terminal cancer, in individual therapeutic treatment and in association with muscle relaxants, pain-killers and central analgesics.

The 2-arylpropionic acids with anti-inflammatory activity of the present invention are made up of highly lipophilic carboxylic acids and as such are scarcely soluble in water. Nonetheless it is possible to prepare solutions of said acids, after salification in aqueous vehicles containing a surplus of a hydrate, of a bicarbonate and/or of an alkaline carbonate or an earth alkaline carbonate such as, for example, sodium hydroxide, sodium bicarbonate, of a preferably basic α-aminoacid or of a hydroxyalkylamine, eventually in the presence of preservatives and excipients and/or dispersing agents.

Said solutions of the 2-arylpropionic acids present a gradual instability easily evidenced from a progressive yellowing, sometimes followed by turbidity and by separation of floccules, phenomena which become more noticeable with a temperature increase and after a prolonged exposure of the solution to light. To overcome said difficulty recourse was made to lyophilized pharmaceutical formulations from which the injectable solution is reconstituted just at the moment of use by means of solubilization in the proper solvent. These solutions contain, furthermore, variable quantities of preserving substances among which the most frequently used are p-hydroxybenzoate of methyl and propyl, and supporting materials in excess such as, for example, glycine, to ensure the volume and compactness of the lyophilized substance itself. The use, together with the active principles, of a ponderal excess of supporting materials results in that the constituted solutions present pH values which vary from 6.5 to 7.3 and are definitely hypertonic. In fact, the osmolarity values measured cover an interval from 650 to 1150 mOsm/kg, which is not very compatible with the isotonicity of biological fluids, which present values comprised between 275 and 295 mOsm/kg. As a result, the administration of such solutions causes pain to the patient and, moreover, superficial liquid effusions can come about. The presence of remarkable quantities of excipients and of the preserving agents in the solution can moreover be the cause of risks deriving from the patient's individual susceptibility to said substances.

It is known that, on the English market, formulations have long been introduced for the extemporaneous use consisting of a ketoprofen solution in a mainly aqueous medium containing an excess of l-arginine, benzylic alcohol and citric acid; said solutions, which present a global pH of about 6.7, are supplied in dark glass containers for a better control of their stability.

The pharmaceutical compositions suitable for parenteral use of the present invention, are made up of aqueous solutions of alkylammonium salt of 2-arylpropionic acids chosen from the group consisting of ketoprofen, ibuprofen, naproxen and tiaprofenic acid in racemic or in enantiomeric form, which present osmolarity values comprised in the range 270–310 mOsm/kg and pH values comprised in the range 7.0–7.5. As alkylammonium bases, bases which include alkyl radicals eventually substituted with hydroxy radicals are used. In the case where the alkylammonium base exists in a racemic or enantiomeric form, the salts can comprise either one or the other of said forms. Bases particularly preferred are α-aminoacids such as lysine and particularly preferred is the salt formed with the forms of said aminoacid having the natural configuration. Another preferred base is the dropropizine or 3-(4-phenyl-1-piperazinyl)-1,2-propanediols. The salifying acid is preferably employed in its racemic form even though salts formed from its separate enantiomers are comprised within the scope of the invention.

The particularly preferred salts are those of (R,S)-ketoprofen with d,l-lysine and with l-lysine respectively described in U.S. Pat. No. 4,279,926 (Jul. 21, 1981) and BE 882,889 (May 14, 1980). Other salts, for example the R- or S-ketoprofen salts with the separated stereoisomers of lysine and dropropizine, are also known and have been described in WO 94/20449 (Sep. 15, 1994).

According to the process of the invention, the pharmaceutical compositions suitable for parenteral use containing salts of a 2-arylpropionic acid selected from the group consisting of ketoprofen, ibuprofen, naproxen and tiaprofenic acid with alkylammonium bases are prepared by solubilizing in an inert-gas atmosphere and away from light, in an aqueous solution, at a pH ranging from 7.0 and 7.5, the alkylammonium salt of the chosen 2-arylpropionic acid.

The use of an inert gas during the preparation of the solutions and their subsequent conservation enable reaching a degree of stability sufficient as to avoid a recourse to the use of preservatives and co-solvents such as, for example, alcohols or glycols for preventing the progressive yellowing of the solutions. Inert gases particularly preferred ate those which are chemically inert with solvents and solutes and are compatible with the foreseen pharmaceutical use: these are, as example, nitrogen and the rare gases helium and argon and their mixtures.

Besides granting the composition of the invention a good tolerability, the lack of benzyl alcohol or other solvent, except water for injectable preparations, also gives the consumer a precise information about the quality of the composition itself. In fact, should the pharmaceutical composition undergo alterations due to an incorrect storage, the appearance of a characteristic whitish opalescence indicates these alterations immediately and therefore the pharmaceutical composition will be not administered. The appearance of said opalescence, which represents a very sensitive index of the pharmaceutical quality of the active principle contained in the composition of the invention, is a guarantee of the quality of the composition, and furthermore, it represents a noticeable improvement with respect to those compositions which contain co-solvent agents, such as in particular benzyl alcohol, and consequently do not make evident the possible presence of alterations which would render the pharmaceutical quality of the composition no longer acceptable.

The packaging, in suitable containers of dark glass optionally disposed in a box wherein each container is separately packaged, as well as the other characteristic of the composition of the invention, assures a full stability of the product as demonstrated by the tests which have been carried out.

Moreover, it has been observed that the pH adjustment of the injectable solution between 7.0 and 7.5 brings about, not only a useful increment of osmolarity towards that degree of hyperosmosis which better than a slight hypo-osmosis adapts itself to a good tolerability of the injectable solution, but also an ulterior improvement in the stability of the darkening solution and in the turbidity whether in tests of thermic accelerated stability or in exposure to light. For the adjustment of the pH and consequently of the osmolarity of the 2-arylpropionic acid salts, mixtures of $C_3$–$C_5$ hydroxy di- and tri-carboxylic acids and the alkaline and alkaline earth salts thereof chosen in the group consisting of the tartronic, malic, tartaric and citric acids have been used. Particularly preferred is the use of citric acid combined with sodium hydroxy and/or sodium citrate.

The dark glass containers are preferably borosilicate phials rendered opaque to light radiations having 290 to 450 nm wave lengths.

Hereunder are given some non-limitative examples of some embodiments of the invention.

EXAMPLE 1

Working sheltered from light, in an atmosphere and under bubbling nitrogen, 37.5 g (c.a.0.195M) of citric acid and 22.5 g (0.5625M) of sodium hydroxide are dissolved in 12 l of sterile, previously de-aerated water for injectable preparations. To the solution so obtained is added under stirring 1.2 kg (3M) of (R,S)-ketoprofen salt of d,l-lysine to control the pH of the solution and eventually adjust it to values varying from 7.0 to 7.5 with additions of sodium hydroxide.

After complete dissolution of the salt, the volume of the solution is brought to 15 ml with sterile, previously de-aerated water for injectable preparations, and stirring is continued for another 15 minutes to ensure the total homogeneity of the solution. Nitrogen is left to bubble in the solution for 15 minutes. Working under pressure and in a nitrogen atmosphere, the solution is filtered through 0.22 micron cartridges, collected in suitable shielded containers appropriately protected from exposure to the UV light radiations and then run into the machine for filling phials for distribution in 2 ml glass ampoules, which are sealed in a nitrogen atmosphere. After sterilization, the single phials are placed in containers which are made to hold one or more phials. If desired, the single phial holders can be protected individually by films which make them opaque to the transmission of light.

EXAMPLE 2

An experiment similar to the experiment described in the preceding Example is carried out by substituting d,l-lysine salt of (R,S)-naproxen for the d,l-lysine salt of (R,S)-ketoprofen. The d,l-lysine salt of (R,S)-naproxen is prepared from 0.2M of d,l-lysine dissolved in 700 ml of water to which is added, after heating to the boiling point temperature, 0.202M of finely sub-divided (R,S)-naproxen. The salt separates from the reaction mixture by removing the water for distillation.

We claim:

1. A pharmaceutical composition suitable for parenteral administration having anti-inflammatory and analgesic properties, comprising an alkylammonium salt of a 2-arylpropionic acid selected from the group consisting of ketoprofen, ibuprofen, naproxen, tiaprofenic acid, in racemic as well as in enantiomeric form, in an aqueous solution having an osmolarity between 270 and 310 mOsm/kg and at a pH in the range between 7.0 and 7.5, said solution being free of preservatives and of supporting substances and being prepared and kept in an inert gas atmosphere and away from light.

2. A pharmaceutical composition according to claim 1, wherein the inert gas is nitrogen.

3. A pharmaceutical composition according to claim 1, wherein the alkylammonium salt of the 2-arylpropionic acid is the d,l-lysine salt of (R,S)-ketoprofen and the inert gas is nitrogen.

4. A pharmaceutical composition according to claim 1, wherein the alkylammonium salt of the 2-arylpropionic acid is the l-lysine salt of (R,S)-ketoprofen.

5. A pharmaceutical composition according to claim 1, wherein the alkylammonium salt of the 2-arylpropionic acid is the l-lysine salt of R-ketoprofen.

6. A pharmaceutical composition according to claim 1, wherein the alkylammonium salt of the 2-arylpropionic acid is the 1-dropropizine salt of R-ketoprofen.

7. A pharmaceutical composition according to claim 1, wherein the alkylammonium salt of the 2-arylpropionic acid is the tromethamine salt of S-ketoprofen.

8. A pharmaceutical composition according to claim 1, wherein the alkylammonium salt of the 2-arylpropionic acid is the tromethamine salt of R-ketoprofen.

9. A pharmaceutical composition according to claim 1, wherein the alkylammonium salt of the 2-arylpropionic acid is the l-lysine salt of S-ketoprofen.

10. A process for the preparation of the pharmaceutical composition according to claim 1, wherein an alkylammonium salt of a 2-arylpropionic acid selected from the group consisting of ketoprofen, ibuprofen, naproxen and tiaprofenic acid is suitably dissolved in water for injectable preparation at a pH between 7.0 and 7.5 in an atmosphere of an inert gas and away from light.

* * * * *